United States Patent [19]

Lindholm

[11] 4,149,010
[45] Apr. 10, 1979

[54] SYNTHESIS OF α-TRIFLUOROMETHYL VINYL ACETATE

[75] Inventor: Edward P. Lindholm, Somerville, Mass.

[73] Assignee: Polaroid Corporation, Cambridge, Mass.

[21] Appl. No.: 811,718

[22] Filed: Jun. 30, 1977

[51] Int. Cl.² ............... C07C 67/00; C07C 67/14; C07C 69/145
[52] U.S. Cl. .................................................. 560/262
[58] Field of Search ....................................... 560/262

[56] References Cited

U.S. PATENT DOCUMENTS 3,444,150   5/1969   Haas et al. ................... 560/262

Primary Examiner—Vivian Garner
Attorney, Agent, or Firm—Esther A. H. Hopkins

[57] ABSTRACT 1,1,1-Trifluoroacetone is acetylated when an excess of an acetylating agent is allowed to react with this ketone in the presence of an excess of an amine such as pyridine.

15 Claims, No Drawings

SYNTHESIS OF α-TRIFLUOROMETHYL VINYL ACETATE

FIELD OF THE INVENTION

This invention is directed to a novel process for the preparation of α-trifluoromethyl vinyl acetate.

BACKGROUND OF THE INVENTION

α-Trifluoromethyl vinyl acetate (2-acetoxy-3,3,3-trifluoropropene) is disclosed and claimed in U.S. Pat. No. 3,444,150 as a novel compound and as a starting monomer for the preparation of homopolymers and copolymers having a variety of uses. Among the copolymers disclosed is vinyl acetate-trifluoromethyl vinyl acetate copolymer, which may be hydrolyzed to vinyl alcohol-α-trifluoromethylvinyl alcohol copolymer, useful in the preparation of photographic processing compositions, as disclosed in U.S. Pat. No. 3,362,822. The homopolymerization of α-trifluoromethyl vinyl acetate, its copolymerization with vinyl acetate and the properties of copolymers so produced and the polyols derived therefrom are further described by Haas, MacDonald and Chiklis in the *Journal of Polymer Science* Part A-1, Vol. 7, pp. 633-641 (1969).

Haas and Schuler, in the *Journal of Polymer Science* Part A, Vol. 2, pp. 1641-1645 (1964) describe the preparation of 3,3,3-trifluoro-2-acetoxypropene (α-trifluoromethyl vinyl acetate) by the dehydrobromination of 3-bromo-2-acetoxy-1,1,1-trifluoropropane prepared from 3-bromo-1,1,1-trifluoro-2-propanol.

In U.S. Pat. No. 3,444,150, the reaction of 1,1,1-trifluoroacetone with trifluoroacetic anhydride to produce α-trifluoroacetoxy-3,3,3-trifluoropropene is disclosed and is given as illustrative of the reaction of

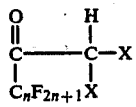

with acid chlorides or anhydrides, where X is hydrogen or halogen preferably fluorine or chlorine. However, the patentees state only that "some monomers" within the scope of their invention may be prepared by this method and the method is not taught or shown to be applicable to the production of α-trifluoromethyl vinyl acetate. Instead, the latter compound is disclosed as being produced by other methods, such as the reaction of 3-bromo-2-acetoxy-1,1,1-trifluoropropane with tributylamine or the reaction of 2-trifluoroacetoxy-3,3,3-trifluoropropene with acetic acid. The method specifically described in U.S. Pat. No. 3,444,150 for the preparation of 2-trifluoroacetoxy-3,3,3-trifluoropropene involves the reaction of 1,1,1-trifluoroacetone with trifluoroacetic anhydride in the presence of potassium acetate in a steel bomb at 100° C. for 16 hours.

Sladkov and Petrov in the *J. General Chemistry U.S.S.R.*, Vol. 24, p. 459 states that the enol acetate of acetaldehyde was obtained by heating the aldehyde with acetic anhydride in the presence of potassium acetate. This method used by Haas and Schuler, *J. Polymer Science* Part A, Vol. 2, pp. 1641 (1964) apparently failed to produce product when applied to trifluoroacetone. They state that they were unable to prepare α-trifluoromethyl vinyl acetate by reacting trifluoroacetone with isopropenyl acetate, vinyl acetate, acetic anhydride or acetyl chloride, "except perhaps in trace quantities," with the use of a variety of acidic and basic catalysts and conditions. It can be concluded that acetylation methods operable for acetaldehyde do not necessarily work for trifluoroacetone. Therefore the teaching of Sladkov and Petrov with respect to the use of an excess of pyridine in the acetylation of acetaldehyde would not lead to the conclusion that trifluoroacetone could be similarly acetylated.

It is an object of this invention to provide an improved method for the preparation of α-trifluoromethyl vinyl acetate.

Other objects of the invention will be apparent hereinafter.

SUMMARY OF THE INVENTION

It has been found that the object of the invention may be accomplished and 1,1,1-trifluoroacetone may be acetylated to obtain α-trifluoromethyl vinyl acetate when an excess of both an acetylating agent and an amine such as pyridine or p-dimethylamino pyridine are allowed to react with this ketone. The reaction is illustrated by the following equation:

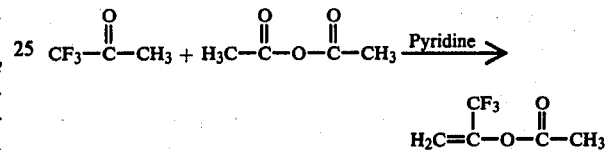

DETAILED DESCRIPTION OF THE INVENTION

The following example illustrates but does not limit the invention:

EXAMPLE 1,1,1-Trifluoroacetone (188.0 g, 1.68 moles, b.p. 21° C.) was evaporated through glass tubing fitted with short tygon connectors and condensed into a tared one liter, 3-neck flask maintained in an ice bath and protected from atmospheric moisture with a Drierite drying tube. The flask was then quickly fitted with a stoppered, pressure-equalizing addition funnel, a thermometer, a condenser with drying tube, and a magnetic stirring bar. With stirring, acetic anhydride (860 g, 8.40 moles) was added over the course of 5 minutes, during which time the temperature rose to about 12°. The ice bath was then removed and pyridine (665 g, 8.40 moles), which had been dried with 4Å molecular sieves, was added over 5 minutes with no noticeable exotherm. The reaction mixture was allowed to warm to room temperature (24° C.) and was stirred slowly for 27 hours. The dark red solution was then poured into 1200 ml of crushed ice followed by the addition of concentrated HCL to acidify the mixture to pH 1-2 as measured with pH paper (approximately 200 g of concentrated HCL were required). The lower organic phase was separated and aqueous phase was extracted with two 100 ml portions of ether. The organic fractions were combined and washed with two 75 ml portions of cold 5% HCl, followed by treatment with cold saturated sodium bicarbonate solution until gas evolution ceased (300 ml), and finally with water. The ether solution was dried over anhydrous magnesium sulfate, filtered, and distilled through a spinning band column. A fraction, collected at 86°-89.5° C., weighed 135.0 gms, which represents a 52% yield. Analysis by vapor phase chromatography showed it to be 99.4 percent pure.

The above example illustrates the reaction carried out at about room temperature (24° C.), but higher and lower temperatures may be employed. The desired product was obtained at reaction temperature as low as about 15° C. and as high as about 50° C., but with decreased yields. Reaction times greater or less than the 27 hours employed in the example may be used. The reaction time, however, should be long enough for the product to be formed and should preferably be at least five hours. p-Dimethylamino pyridine may be substituted for pyridine in which case the reaction is speeded up but the yield is not increased. Molar proportions of acetylating agent to 1,1,1-trifluoroacetone to amine other than those shown in the example (1 to 0.2 to 1, respectively) may be employed, provided there is an excess of both amine and acetylating agent with respect to the 1,1,1-trifluoroacetone. Different molar proportions reduce the yield of the α-trifluoromethyl vinyl acetate. For example, the use of molar proportions of 2:1:2 resulted in a ten percent lowering of the yield of purified material. Instead of acetic anhydride, other acetylating agents such as, for example, acetyl chloride may be employed.

Numerous modifications and variations of the present invention are possible in light of the above teachings, and accordingly, within the scope of the appended claims the invention may be practiced in a manner other than as particularly described.

What is claimed is:

1. A process which comprises reacting, at a temperature from about 15° C. to about 50° C., 1,1,1-trifluoroacetone with an acetylating agent in the presence of an amine selected from the group consisting of pyridine and p-dimethylamino pyridine, said acetylating agent and said amine being in molar excess with respect to said 1,1,1-trifluoroacetone, for a time sufficient to form α-trifluoromethyl vinyl acetate.

2. The process of claim 1 wherein the reaction is carried out at approximately 24° C.

3. The process of claim 1 wherein said amine is pyridine.

4. The process of claim 1 wherein the reaction is carried out for at least five hours.

5. The process of claim 1 wherein said acetylating agent is acetic anhydride.

6. The process of claim 5 wherein the reaction is carried out at approximately 24° C.

7. The process of claim 5 wherein the reaction is carried out for a period of at least five hours.

8. The process of claim 5 wherein said amine is pyridine.

9. The process of claim 5 wherein said amine is p-dimethylamino pyridine.

10. The process of claim 5 wherein the molar proportions of acetylating agent to 1,1,1-trifluoroacetone to amine are about 2:1:2, respectively.

11. The process of claim 5 wherein the molar proportions of acetylating agent to 1,1,1-trifluoroacetone to amine are about 1 to 0.2 to 1, respectively.

12. The process of claim 11 wherein said amine is pyridine.

13. The process of claim 12 wherein the reaction is carried out for a period of at least five hours.

14. The process of claim 12 wherein the reaction is carried out at approximately 24° C.

15. The process for the preparation of α-trifluoromethyl vinyl acetate which comprises reacting for approximately 27 hours at approximately 24° C. 1,1,1-trifluoroacetone with acetic anhydride in the presence of pyridine, the molar proportions of acetic anhydride to 1,1,1-trifluoroacetone to pyridine being about 1 to 0.2 to 1, respectively.

* * * * *